United States Patent
Huculak et al.

(10) Patent No.: US 9,517,162 B2
(45) Date of Patent: Dec. 13, 2016

(54) RETINAL SURGERY

(75) Inventors: John Christopher Huculak, Mission Viejo, CA (US); Michael McCulloch Martin, Newport Beach, CA (US); Michael Arthur Zica, Costa Mesa, CA (US); Matthew Edward Bazydlo, Costa Mesa, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 0 days.

(21) Appl. No.: 13/307,658

(22) Filed: Nov. 30, 2011

(65) Prior Publication Data

US 2013/0138035 A1 May 30, 2013

(51) Int. Cl.
*A61F 9/008* (2006.01)
*A61M 1/00* (2006.01)
*A61F 9/007* (2006.01)

(52) U.S. Cl.
CPC ....... *A61F 9/00821* (2013.01); *A61F 9/00736* (2013.01); *A61M 1/0031* (2013.01); *A61M 1/0058* (2013.01); *A61F 9/00727* (2013.01); *A61M 2205/3344* (2013.01); *A61M 2210/0612* (2013.01); *F04C 2270/041* (2013.01)

(58) Field of Classification Search
CPC .............. A61F 9/00727; A61F 9/00736; A61F 9/00821; A61M 1/0031; A61M 1/0058; A61M 2205/3344; A61M 2210/0612
See application file for complete search history.

(56) References Cited

U.S. PATENT DOCUMENTS

| 4,490,351 | A | | 12/1984 | Clark, Jr. |
| 5,358,473 | A | * | 10/1994 | Mitchell ............. A61F 9/00736 604/27 |
| 6,098,466 | A | | 8/2000 | Shkarlet |
| 6,117,149 | A | * | 9/2000 | Sorensen et al. ............. 606/166 |
| 6,251,113 | B1 | * | 6/2001 | Appelbaum et al. ......... 606/107 |
| 6,290,690 | B1 | * | 9/2001 | Huculak et al. ............. 604/521 |
| 7,326,183 | B2 | | 2/2008 | Nazarifar et al. |
| 7,713,237 | B2 | | 5/2010 | Nazarifar et al. |

(Continued)

FOREIGN PATENT DOCUMENTS

CN 101932348 8/2013
CN 102245222 5/2014

(Continued)

OTHER PUBLICATIONS

Medone Surgical, Inc., "MedOne: New Products" (online), (retrieved from www.medone.com/pdf/MedOne%20New%20Products%202007-2008.pdf), 2008 (retrieved on Sep. 25, 2011) (2 pages).

(Continued)

*Primary Examiner* — Imani Hayman
(74) *Attorney, Agent, or Firm* — Haynes and Boone, LLP (57) ABSTRACT

Systems, processes, and computer program products may be used to perform retinal surgery. In particular implementations, a system, a process, and a computer program product may include the ability to inject a retina manipulation fluid into an eye through an injection/extraction system and apply negative pressure to the injection/extraction system to facilitate extraction of fluid from the eye. The system, the process, and the computer program product may also include the ability to adjust the applied negative pressure.

19 Claims, 4 Drawing Sheets

(56) References Cited

U.S. PATENT DOCUMENTS

| | | | |
|---|---|---|---|
| 7,758,538 | B2 | 7/2010 | Boukhny et al. |
| 7,786,457 | B2 | 8/2010 | Gao |
| 7,896,839 | B2 | 3/2011 | Nazarifar et al. |
| 8,006,570 | B2 | 8/2011 | Nazarifar et al. |
| 2002/0095113 | A1 | 7/2002 | Kishimoto |
| 2008/0172078 | A1* | 7/2008 | Svetic .......................... 606/171 |
| 2008/0208207 | A1 | 8/2008 | Huculak et al. |
| 2009/0247938 | A1 | 10/2009 | Buboltz |
| 2010/0191176 | A1 | 7/2010 | Ho et al. |
| 2012/0053486 | A1* | 3/2012 | Huculak .............. A61B 3/0025 600/573 |

FOREIGN PATENT DOCUMENTS

| | | |
|---|---|---|
| JP | 2004-507321 | 3/2004 |
| JP | 3529311 | 5/2004 |
| JP | 3845013 | 11/2006 |
| JP | 2010-246573 | 11/2010 |
| JP | 2011-512165 | 4/2011 |
| WO | WO 02/17833 | 3/2002 |

OTHER PUBLICATIONS

Microvision Incorporated, "Product Catalog" (online), (retrieved from www.micro-vision.net/documents/catalog.pdf), Jul. 2011 (retrieved on Sep. 26, 2011) (24 pages).

International Search Report and Written Opinion for PCT/US2012/051874, Publication No. WO2013/081690, dated Nov. 2, 2012, 7 pages.

Extended European Search Report and Annex to the European Search Report issued for EP Application No. 12853898 dated Sep. 9, 2014, 7 pgs.

Patent Examination Report No. 2, issued for AU 2012346522, dated Feb. 4, 2015, 5 pgs.

English Translation of Japanese Office Action issued for Japanese Application No. 2014-544727, dated May 12, 2015, 3 pgs.

European Examination Report issued for EP Application No. 12853898, dated May 21, 2015, 5 pgs.

English Translation of Chinese Office Action issued for Chinese Application No. 201280058813.5, dated Jul. 6, 2015, 12 pgs.

English Translation of Japanese Office Action issued for Japanese Application No. 2014-544727, dated Aug. 3, 2015 (mailing dated of Aug. 11, 2015), 2 pgs.

* cited by examiner

RETINAL SURGERY

BACKGROUND

The present disclosure relates to optical surgery, and more specifically to surgery on a patient's retina.

The human eye, in simple terms, functions to provide vision by transmitting and refracting light through a clear outer portion called the cornea and focusing the image by way of the lens onto a light-sensitive tissue lining the inner surface called the retina. The quality of the focused image depends on many factors including the size, shape, and length of the eye, and the shape and transparency of the cornea and lens.

Unfortunately, trauma, age, or disease may cause the retina to peel away from its support tissue, often termed retinal detachment. Retinal detachment is more common among those with severe myopia, but may also occur as a result of physical trauma to the eye, cataract surgery, or diabetic retinopathy. Initial detachments may be localized, but without rapid treatment, the entire retina may detach, leading to vision loss and blindness.

BRIEF SUMMARY

In one general implementation, a process for retinal surgery may include injecting a retina manipulation fluid into an eye through an injection/extraction system and applying negative pressure to the injection/extraction system to facilitate extraction of fluid from the eye. The injection/extraction system may, for example, be a dual bore cannula having a port for the inner bore. The process may also include adjusting, via a computer system, the applied negative pressure.

The applied negative pressure may, for example, be adjusted based on intraocular pressure (interchangeably referred to herein as "IOP") of the eye. Some implementations may also include measuring the IOP. In certain implementations, the process may include injecting fluid to maintain the shape of the eye.

The injection of the retina manipulation fluid through injection/extraction system may, for example, be controlled via the computer system. The computer system may, for instance, control a fluid pressure system to apply positive pressure to inject the retina manipulation fluid.

In certain implementations, injecting a retina manipulation fluid through an injection/extraction system may include injecting the retina manipulation fluid through a first channel, and extracting fluid from the eye may include extracting fluid through a second channel. The extracted fluid may, for example, be extracted around the first channel. The second channel may, for instance, serve as a cannula for introducing medical instruments into an eye. In some implementations, the retina manipulation fluid, while in the first channel, may pass through an internal cavity of the injection/extraction system. In particular implementations, the extracted fluid enters the cavity after passing through the second channel.

Various implementations may include one or more features. For example, by being able to monitor the pressure in an eye undergoing surgery and adjust extraction of fluid through an injection/extraction system, an appropriate pressure may be obtained in eye. If eye pressure becomes too low, the eye may collapse, and if eye pressure becomes too high, blood may be cut off to the eye. As another example, in certain implementations, a larger bore may be available for the injection/extraction device, which may allow more fluid to be injected with a lower pressure drop, which may reduce jetting effects.

The details and features of various implementations will be conveyed by the following description, along with the drawings.

DETAILED DESCRIPTION

Figure 1:
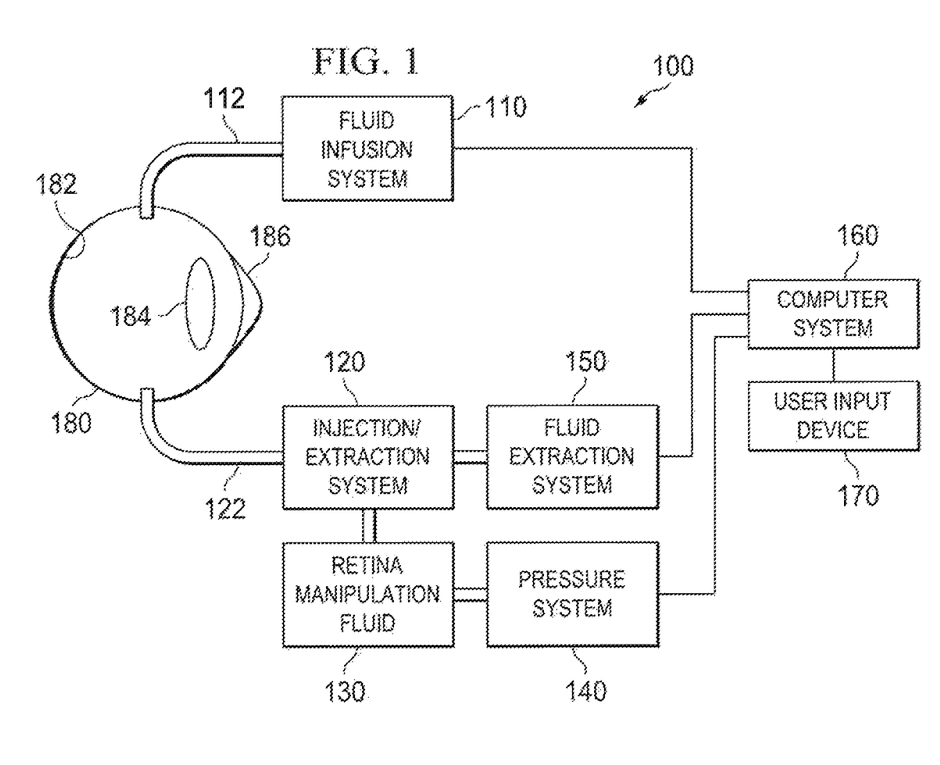
FIG. 1 is a block diagram illustrating an example system for retinal surgery.

FIG. 1 illustrates an example system 100 for retina surgery. System 100 includes a fluid infusion system 110, a fluid injection/extraction system 120, a retina manipulation fluid source 130, a pressure system 140, and a fluid extraction system 150. Fluid infusion system 110, pressure system 140, and fluid extraction system 150 are controlled by a computer system 160, which receives input from a user input device 170. System 100 is adapted to assist in performing surgery on a retina 182 of an eye 180, which also includes a cornea 186 and a lens 184, by delivering one fluid to maintain the eye's shape and another fluid to assist in the manipulation of retina 182. Note that some eyes do not contain a lens, but this should typically not interfere with the operations of system 100.

Fluid infusion system 110 is adapted to supply a fluid (e.g., a saline solution or air) into eye 180 to maintain its shape. In some implementations, the fluid may be injected into eye 180 at approximately 0-3.9 psi, although pressures up to 15 psi may be possible. The infusion fluid may be delivered to eye 180 through a channel 112, which may, for example, include silicone tubing and an eye probe (e.g., an infusion cannula). Typically, the infusion fluid is delivered throughout a surgery as the eye may steadily lose fluid (e.g., due to incisions). Infusion system 110 may include a pump and a fluid source, which may be managed by a local computer system in conjunction with computer system 160. The local computer system may, for example, be a controller printed circuit board. In certain implementations, fluid infusion system 110 may be a subsystem of a fluidics module of a surgical console.

Fluid infusion system 110 may also be adapted to measure intraocular pressure in eye 180. For example, infusion system 110 may measure the flow of fluid into eye 180 and determine the pressure drop in channel 112. Measuring the fluid flow may, for example, be accomplished using non-invasive ultrasonic techniques (e.g., by using piezo-electric crystals). The IOP may be the infusion pressure minus the pressure drop in channel 112 at the currently measured infusion flow rate. The pressure may be reported to computer system 160. In some implementations, a pressure transducer could be inserted directly into the eye to measure the IOP.

Injection/extraction system 120 is adapted to inject a retina manipulation fluid 130 into eye 180 and extract other fluids (e.g., saline solution). Retina manipulation fluid 130 may, for example, have a relatively high specific gravity and therefore sink to retina 182. In cases where retina 182 is detached, the retina manipulation fluid may move retina 182 towards the back of eye 180 (e.g., due to surface tension), where it may be repaired. An example fluid with high specific gravity is perfluorocarbon. The relatively high specific gravity fluid may also cause a lower specific gravity fluid (e.g., saline solution) to rise, at which point it may be extracted. In particular implementations, injection/extraction system 120 may be a dual-bore cannula, which will be discussed in more detail below. Retina manipulation fluid 130 may, for example, be stored in a vial and pressurized through a syringe-like mechanism.

Pressure system 140 is adapted to pressurize retina manipulation fluid 130 to deliver it to injection/extraction system 120. Pressure system 140 may, for example, include a hospital air supply system or a tank (e.g., filled with nitrogen). Pressure system 140 may also include a regulator to lower the pressure. In certain implementations, the pressure may be regulated down from 120 psi to between 0-80 psi, which may be controllable by a user (e.g., physician or other medical professional). The pressure from pressure system 140 is then used to drive the retina manipulation fluid, which may, for example, arrive at injection/extraction system 120 with a pressure between 0-15 psi and be delivered into the eye at a pressure between 0-3.9 psi.

Fluid extraction system 150 is adapted to actively remove fluid through injection/extraction system 120. Extraction system 150 may, for example, accomplish this by using negative pressure, which may be produced by a pump. The extracted fluid may, for instance, be stored in a bag, which may be thrown away after a surgery. In certain implementations, fluid extraction system 150 may be a subsystem of a fluidics module of a surgical console.

Computer system 160 is adapted to control system 100. Computer system 160 may, for example, include a processor (e.g., a microprocessor or microcontroller) and memory (e.g., solid-state and/or disc), which may store data and instructions (e.g., programs) on which the processor operates.

In certain implementations, computer system 160 may store programs for other parts of system 100 and download the programs to individual modules (e.g., during system boot up). Computer system 160 may also monitor activity (e.g., intraocular pressure) so it can send data to user output devices (e.g., a display module).

Computer system 160 may receive inputs from user input device 170. User input device 170 may, for example, be a keyboard, a keypad, a pointing device (e.g., stylus or mouse), or a switch (e.g., a footswitch). Note that although only one user input device is shown, a computer system may have a number of user input devices.

In certain modes of operation, computer system 160 may instruct infusion system 110 to begin injecting fluid into eye 180 as surgery proceeds. The amount of injected fluid may, for example, be established by a user (e.g., a physician). The computer system associated with infusion system 110 may receive feedback from infusion system 110, determine IOP of eye 180, and adjust the amount of fluid being injected. For instance, if the IOP is determined to be decreasing, more fluid may be injected.

Computer system 160 may also receive a command (e.g., from user input device 170) to inject retina manipulation fluid 130 into eye 180. Computer system 160 may accordingly command pressure system 140 to apply pressure, which may advance retina manipulation fluid 130 to injection/extraction system 120. The injection/extraction system 120 passes the retina manipulation fluid 130 through channel 122 and injects the retina manipulation fluid into eye 180. Retina manipulation fluid 130 may fill between 0-90 percent of the eye.

Computer system 160 may also monitor the IOP of eye 180 and instruct extraction system 150 to increase or decrease negative pressure (e.g., suction). For example, computer system 160 may monitor IOP based on feedback from infusion system 110. In some instances, if the IOP is increasing, negative pressure may be increased to draw more fluid through injection/extraction system 120. On the other hand, if the IOP is decreasing, negative pressure may be decreased to draw less fluid through injection/extraction system 120. Normal IOP is typically between 10-20 mmHG, but during surgery, the IOP can range from 0-60 mmHg.

During a surgery, computer system 160 may also receive a command to adjust the amount of retina manipulation fluid being injected into eye 180 (e.g., based on a command from user input device 170). Computer system 160 may accordingly command pressure system 140 to adjust the pressure of the retina manipulation fluid. An adjusting command may also be sent to extraction system 150. In particular implementations, if the pressure from system 140 is being adjusted to zero, the pressure being exerted by extraction system 150 may also be set to zero.

After a sufficient amount of retina manipulation fluid has been applied, a user may perform other procedures on retina 182. For instance, for a detached retina, a physician may apply a number of laser shots to the retina (e.g., pan retinal photocoagulation) to seal the retina to the back of the eye. The physician may also insert another fluid (e.g., air or silicone oil) into the eye to facilitate holding the retina in place. Some of these fluids (e.g., air) may dissipate over time (e.g., days, weeks, or months).

System 100 has a variety of features. For example, by being able to monitor the IOP of eye 180 and adjust extraction of fluid through injection/extraction system 120, a desired IOP may be obtained in eye 180. If the IOP gets too low, the eye may collapse, and if the IOP is too high, blood may be cut off to the eye. Existing dual-bore cannula rely on the pressure differential between pressure within the eye 180 and atmospheric pressure to purge fluids during injection of a retina manipulation fluid, which can result in harmful increases in IOP as the cannula are capable of delivering much higher flow rates than they can passively purge. Moreover, although they may back-drive fluid up the infusion line for some systems in an attempt to maintain IOP, this may fail if the infusion channel is occluded or may result in saturation of the infusion line filter, resulting in a loss of IOP control.

Although FIG. 1 illustrates one implementation of a system for retinal surgery, other systems for retinal surgery may have fewer, additional, and/or a different arrangement of components. For example, infusion system 110, extraction system 150, and computer system 160 may be part of a unit. For instance, they may be part of a vitreoretinal surgical console, such as, for example, the Constellation® Vision System available from Alcon Laboratories, Inc., of Fort Worth, Tex. As another example, some of the functions of computer system 160 (e.g., controlling the extraction pressure applied to injection/extraction system 120) may be performed by other computer systems (e.g., a computer system in a fluidics module).

As a further example, a system may not make and/or use an IOP measurement. For instance, a table stored in memory could be created with a set extraction levels associated with retina manipulation fluid injection pressures. In certain implementations, for example, the amount of fluid extracted could be approximately equal to the amount of retina manipulation fluid injected.

Figure 2:
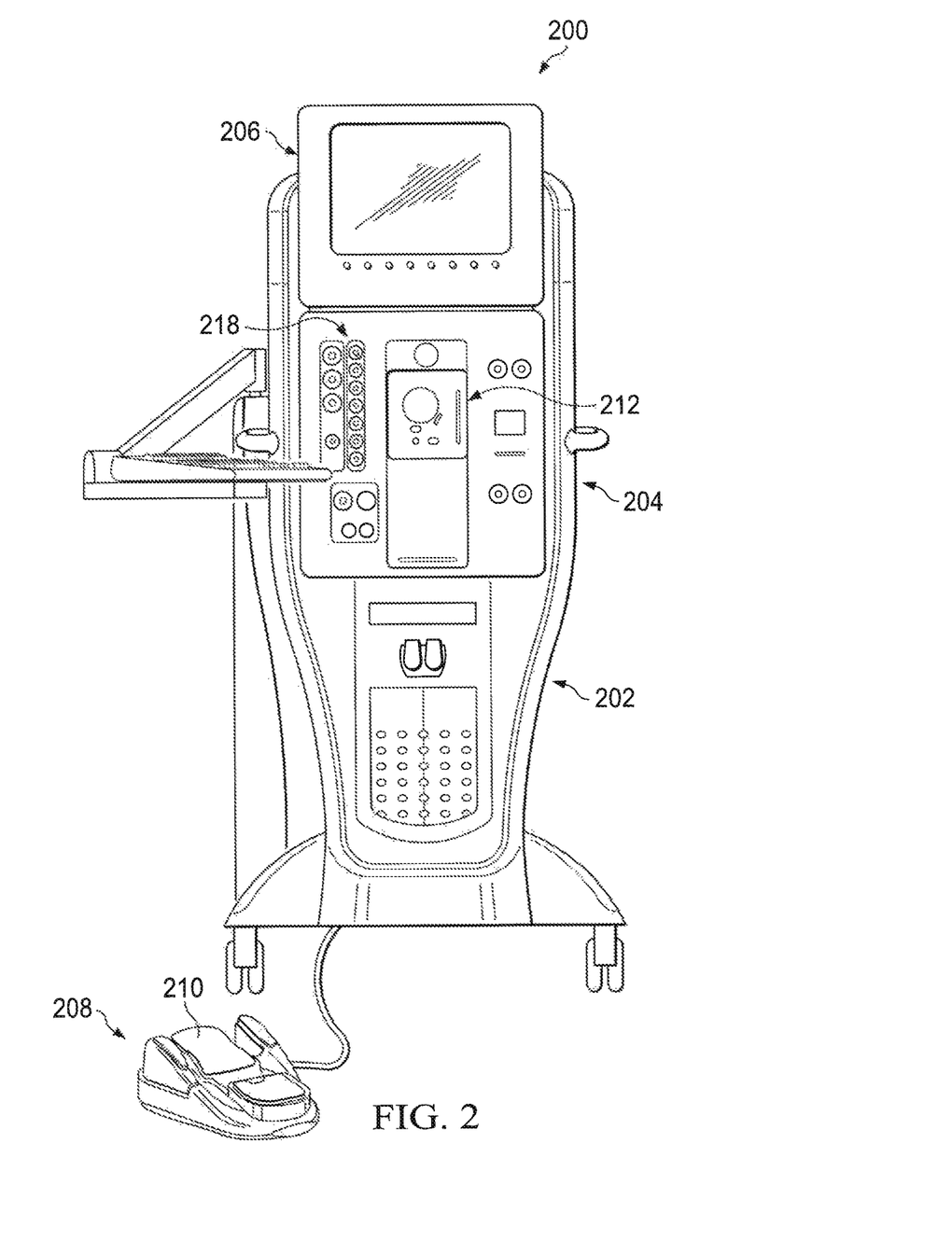
FIG. 2 shows an example surgical console for retinal surgery.

FIG. 2 illustrates an example surgical console 200 for retinal surgery. Console 200 includes a housing 202 with a computer system 204 and an associated display 206 operable to show, for example, data relating to system operation and performance during a vitreoretinal surgical procedure. Display 206 may also interface with the console, such as to establish or change one or more operations of the console. In some instances, display 206 may include a touch-sensitive screen for interacting with the console by touching the screen of the display 206.

Various probes may be used with surgical console 200. A probe, such as, for example, a vitrectomy probe, may be coupled to console 200 for dissecting ocular tissues and aspirating the ocular tissues from the eye. Other probes may, for example, introduce fluids to and/or extract fluids from the eye. Console 200 may, for example, provide electrical, pneumatic, hydraulic, and/or other appropriate type of power to a probe. Console 200 may also be operable to control the supplied power (e.g., an infusion rate of fluid to a surgical site and/or aspiration of fluid from a surgical site), as well as to monitor one or more patient vital signs.

Console 200 may also include a number of systems that are used together to perform vitreoretinal surgical procedures. For example, the systems may include a footswitch system 208 including, for example, a footswitch 210, a fluidics system 212, and a pneumatics system 218. The pneumatics system 218 may be operable to supply power to and control a probe. For example, the pneumatics system 218 may be operable to repeatedly cycle application of a pressurized gas. In some instances, the pneumatic system 218 may be operable to cycle pressurized gas at rates within the range of one cycle per minute to 7,500 cycles per minute, or possibly even 10,000 cycles per minute or more. In certain implementations, the cycled gas may be applied at, for example, different pressures, different rates, and different duty cycles. A probe may be interfaced With console 200 via pneumatics system 218 (e.g., to control actuation of a cutter). Fluidics system 212 may be operable to provide infusion and/or irrigation fluids to the eye or a vacuum, such as to aspirate materials during a surgical procedure. To optimize performance of the different systems during surgery, their operating parameters may be varied according to, for example, the particular procedure being performed, the different stages of the procedure, the surgeon's personal preferences, whether the procedure is being performed in the anterior or posterior portion of the patient's eye, and so on.

The different systems in console 200 may include control circuits for the operation and control of the various functions and operations performed by the console 200, such operations of a probe. Computer system 204 may be operable to govern the interaction and relationship between the different systems to properly perform a surgical procedure. To do this, computer system 204 may include one or more processors, one or more memory devices, and may be configured or programmed to control operations of the console 200, for example, based upon pre-established programs or sequences.

Figure 3:
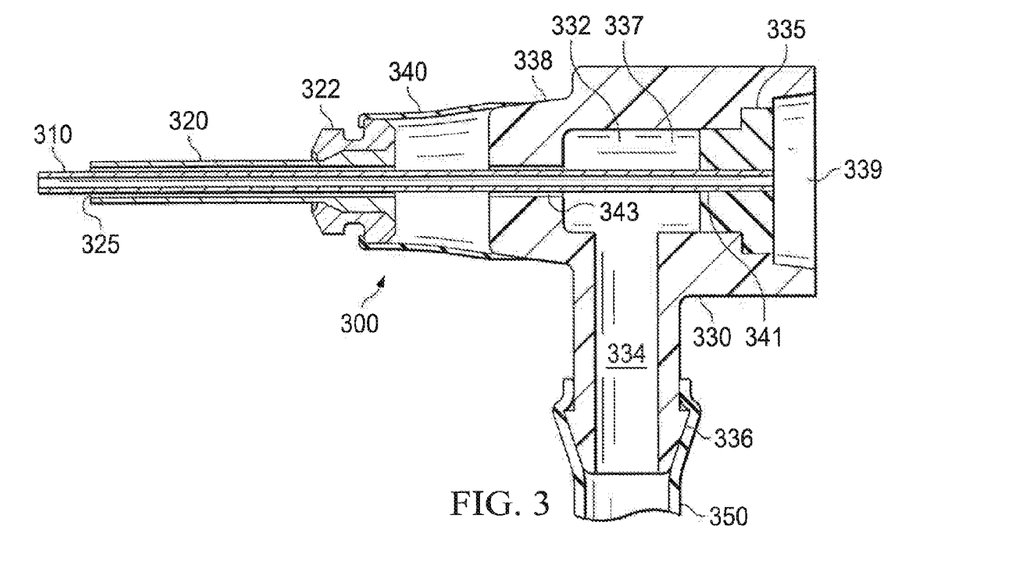
FIG. 3 shows an example injection/extraction system for retinal surgery.

FIG. 3 illustrates an example injection/extraction system 300 for retinal surgery. System 300 may, for example, be useable in a retinal surgery system like system 100.

System 300 includes a first cannula 310 and a second cannula 320. First cannula 310 is adapted to serve as a channel to inject a retina manipulation fluid into an eye. An annular region defined between the first cannula 310 and the second cannula 320 defines a channel 325 through which fluid is extracted from the eye.

In the illustrated implementation, first cannula 310 is inside second cannula 320. Additionally, first cannula 310 extends beyond second cannula 320. When the retina manipulation fluid is of a higher specific gravity than the fluid in the eye, the retina manipulation fluid sinks to a low position within the eye, causing the pre-existing eye fluid, which is of a lower specific gravity, to rise. As a result, the pre-existing eye fluid may be extracted from the eye via the channel 325. First cannula 310 may extend farther than second cannula 320 by varying amount depending on application.

In some instances, the second cannula 320 may be or operate as a trocar cannula. Thus, as shown in the illustrated example of FIG. 3, the second cannula 320, when installed in an eye, defines a passageway used to provide communication between the interior and the exterior of an eye. Generally, the passageway of a trocar cannula may be used to introduce items, such as materials or instruments into the eye. Accordingly, the second cannula 320 may be used to introduce the first cannula 310 into the eye. Second cannula 320 includes a hub 322, which limits an amount by which second cannula 320 penetrates into an eye.

First cannula 310 and second cannula 320 may be made of any appropriate materials. In particular implementations, first cannula 310 may be made of polyimide, and second cannula 320 may be made of stainless steel. First cannula 310 could also be made of other materials (e.g., stainless steel), and second cannula 320 could also be made of other materials (e.g., polyimide).

System 300 also includes a body 330. Body 330 includes a chamber 332. A partition 335 may be formed or otherwise disposed in the chamber 332, dividing the chamber 332 into a first chamber portion 337 and a second chamber portion 339. The first cannula 310 extends through a passage 341 formed in the partition 335. A retinal manipulation fluid present in the second chamber portion 339 may be introduced into the eye via first cannula 310. Fluid may be extracted from the eye via channel 325 defined by first cannula 310 and second cannula 320. The extracted fluid passes through the channel 325 and passageway 343 and enters the first chamber portion 337. The first chamber portion 337 is coupled to a passage 334, which leads to a tube 350 through which negative pressure may be applied to second cannula 320. Thus, the extracted fluid may be evacuated from the body 300 via the tube 350. The body 330 may also include an attachment mechanism 336 (a tapered annular boss in this implementation) for engaging tube 350. Tube 350 may be made of rubber, plastic, or any other appropriate material.

Body 330 may be made of any appropriate material. In particular implementations, body 330 may be made of plastic, such as, for example, polypropylene. In particular implementations, body 330 and first cannula 310 may be an integral unit.

Body 330 is coupled to second cannula 320 by a sleeve 340. In the illustrated implementation, sleeve 340 engages a portion of hub 322 of second cannula 320 and a hub 338 of body 330 to achieve the coupling.

In particular implementations, sleeve 340 may be flexible so that the insertion depth of first cannula 310 may be adjusted. For instance, in the illustrated implementation, sleeve 340 may be adjusted relative to hub 338 along the longitudinal axis of first cannula 310.

Sleeve 340 may be made of any appropriate material. In certain implementations, sleeve 340 may be made of elastomeric tubing (e.g., silicone rubber).

System 300 has a variety of features. For example, by using a trocar cannula as the second cannula 320, system 300 has a larger extraction bore, which may allow more fluid to be extracted at a lower pressure. Additionally, the larger extraction bore may allow first cannula 310 to have a larger bore, which can allow a higher flow with a lower pressure drop and thereby decrease jetting effects.

Although FIG. 3 illustrates one implementation of an injection/extraction system, other implementations may include fewer, additional, and/or a different arrangement of components. For example, instead of using a trocar cannula as the second cannula 320, a dual bore cannula may be used. The dual bore cannula may, for example, be inserted into the eye through a trocar cannula.

Figure 4:
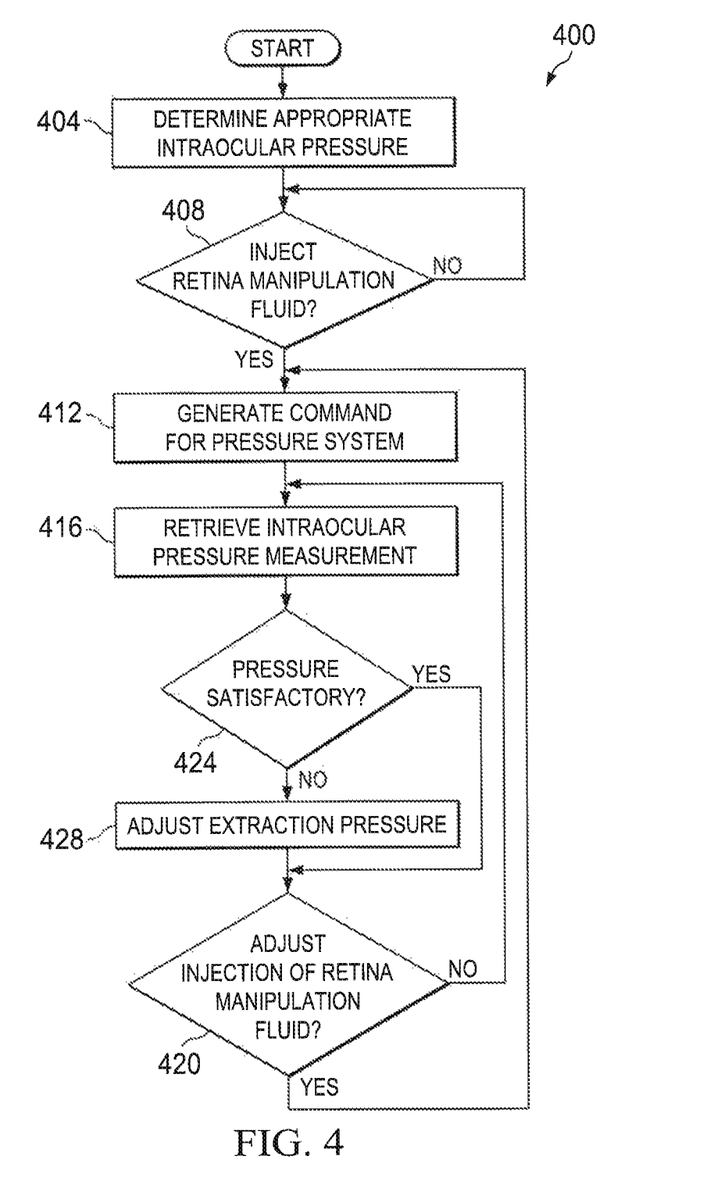
FIG. 4 is a flow diagram illustrating an example process for retinal surgery.

FIG. 4 illustrates a process 400 for retinal surgery. Process 400 may, for example, be implemented by a system like system 100 at the beginning or during retinal surgery.

Process 400 calls for determining a desired intraocular pressure (operation 404). The desired IOP may be used as a target at which IOP is to be maintained. Determining a desired IOP may, for example, be accomplished by receiving an IOP through a user interface or retrieving it from storage. The IOP may, for example, be set by a user (e.g., a physician) before a procedure begins.

Process 400 also calls for determining whether to inject a retina manipulation fluid (operation 408). A retina manipulation fluid (e.g., perfluorocarbon) may, for example, be injected upon receiving a user command (e.g., from a physician).

Once it is determined that a retina manipulation fluid should be injected, process 400 calls for generating a command for a pressure system (operation 412). The pressure system (e.g., a hospital air supply system) may cause the fluid to be injected through an injection/extraction system. The command may be sent over a bus, local area network, or other appropriate communication network. Additional commands may adjust the pressure from the pressure system during a surgery.

Process 400 also calls for retrieving an IOP measurement (operation 416). An IOP measurement may, for example, be made by determining the pressure drop in an infusion channel or by a probe inserted into an eye. Process 400 further calls for determining whether the IOP is satisfactory (operation 424). The IOP may, for example, be satisfactory if it is within a certain range (e.g., 10%) of the desired IOP. If the IOP is satisfactory, process 400 calls for checking whether an adjustment for the injection of the retina manipulation fluid should be made (operation 420). An adjustment may, for example, be made based upon a received user command.

If, however, the IOP is not satisfactory, process 400 calls for adjusting extraction pressure for a fluid injection/extraction system (operation 428). Extraction pressure may, for example, be increased if the measured IOP is too high and decreased if the measured IOP is too low. The extraction pressure may, for example, range between 0-650 mmHg and may, for instance, be placed at zero if the retina manipulation fluid is no longer being injected. Process 400 also calls for calls for checking whether an adjustment for the injection of the retina manipulation fluid should be made (operation 420). An adjustment may, for example, be made based upon a received user command.

If an adjustment for the injection of the retina manipulation fluid should not be made, process 400 calls for retrieving the IOP measurement (416), which may or may not have been updated since the previous IOP measurement. If an adjustment for the injection of the retina manipulation fluid should be made, process 400 calls for generating a command for the pressure system (operation 412).

Although FIG. 4 illustrates one implementation of a process for retinal surgery, other processes may include fewer, additional, and/or a different arrangement of operations. For example, a process may not include checking whether to inject a retina manipulation fluid. Moreover, a process may not even include injection of a retina manipulation fluid. As another example, a process may include injecting an infusion fluid. As an additional example, a process may call for manipulation of various probes. As a further example, a process may not call for using an IOP measurement. For instance, a table stored in memory with a set extraction levels associated with retina manipulation fluid injection pressures may be used to control fluid extraction. In certain implementations, for example, the amount of fluid extracted could be approximately equal to the amount of retina manipulation fluid injected.

As will be appreciated by one skilled in the art, aspects of the present disclosure may be implemented as a system, method, or computer program product. Accordingly, aspects of the present disclosure may take the form of an entirely hardware environment, an entirely software embodiment (including firmware, resident software, micro-code, etc.), or an implementation combining software and hardware aspects that may all generally be referred to herein as a "circuit," "module," or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of a computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this disclosure, a computer readable storage medium may be a tangible medium that can contain or store a program for use by or in connection with an instruction execution system, apparatus, or device.

A computer readable signal medium may include a propagated data signal with computer readable program code embodied therein, for example in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any medium, including but not limited to wireless, wireline, optical fiber cable, RF, etc. or any suitable combination of the foregoing.

Computer program code for carrying out operations for aspects of the disclosure may be written in any combination of one or more programming languages such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer, or entirely on the remote computer or server. In the latter scenario, the remote computer may be connected to the user's computer through any type of network, including a local area network (LAN), a wide area network (WAN), or a wireless network (e.g., Wi-Fi or cellular), or the connection may be made to an external computer (for example, through the Internet using an Internet Service Provider).

Aspects of the disclosure are described with reference to flowchart illustrations and/or block diagrams of methods, apparatus (systems), and computer program products according to implementations. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other device to function in a particular manner, such that the instructions stored in the computer readable medium produce an article of manufacture including instructions that implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus, or other devices to produce a computer implemented process such that the instructions that execute on the computer or other programmable apparatus provide processes for implementing the functions/acts specified in the flowchart and/or block diagram block or blocks.

Figure 5:
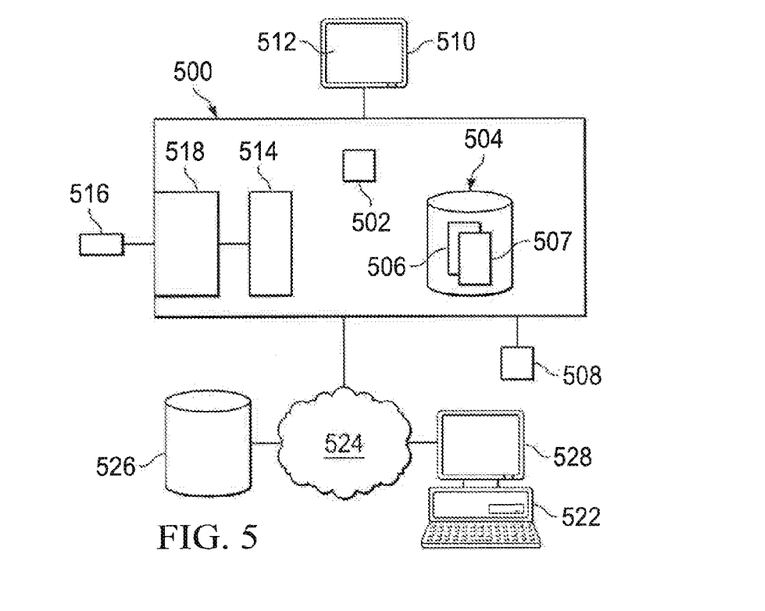
FIG. 5 is a block diagram illustrating an example computer system for retinal surgery.

FIG. 5 illustrates an example computer system 500 for retina surgery. Computer system 500 may, for example, be similar to computer system 160 in system 100 or a computer system that is part of another subsystem (e.g., a fluidics module). Further, in some implementations, the computer system 500 may be a surgical console similar to console 200. In other instances, the computer system 500 may form a part of a surgical console. For example, in some instances, computer system 500 may include or form a part of a computer system of a console, such as, for example, computer system 204 of console 200. In some implementations, computer system 500 may be composed of a number of computer systems (e.g., a distributed computer system).

While an example computer system is shown in FIG. 5, other implementations of a computer system may include more, fewer, or different components than those shown.

Computer system 500 includes a processor 502 and memory 504. Computer system 500 may also include one or more input devices 508, and one or more output devices, such as a display 510. Display 510 may present a user interface or an application interface (collectively referred to as "user interface 512"), discussed in more detail below. A user may interface with user interface 512 to interact with one or more features of the computer system 500. In certain implementations, user interface 512 may be a graphical user interface. Input device(s) 508 may include a keypad, a touch screen, a pointing device (e.g., a mouse or a stylus), a foot-operated input device (e.g., a footswitch), or any other desired input device.

Additionally, computer system 500 includes an operations portion 514. In some instances, operations portion 514 may include a system similar to the system 100 described above. For example, the operations portion 514 may include one or more of an injection/extraction system, a fluid extraction system, a pressure system similar, and a fluid infusion system. The injection/extraction system may be similar to the injection/extraction system 120. The fluid extraction system may be similar to the fluid extraction system 150. The pressure system may be similar to the pressure system 140, and the fluid infusion system may be similar to the fluid infusion system 110.

The system 500 may also include, whether included in the operations portion 514 or in another portion of the system 500, an amount of retina manipulation fluid. In other implementations, an amount of retina manipulation fluid may be remote from system 500. Further, in some implementations, the operations portion 514 include a power source for a vitrectomy probe, aspiration components, irrigation components, as well as one or more sensors, pumps, valves and/or other components for operating a probe. Probe 516 may be coupled to the operations portion 514 of computer system 500 via an interface panel 518 and be supplied with hydraulic, pneumatic, and/or electrical power. In some instances, probe 516 may be a vitreoretinal probe, a fluid injection/extraction system (e.g., the injection/extraction system 300), or any other suitable device. Further, in some implementations, the operations portion 514 may include some of the above-described features and not others. Still further, the operations portion 514 may include one or more additional features other than one or more of the features described herein.

Processor 502 typically includes a logical processing unit (e.g., an arithmetic logic unit) that processes data under the direction of program instructions (e.g., from firmware and/or software). For example, processor 502 may a microprocessor, a microcontroller, or an application specific integrated circuit. In general, processor 502 may be any device that manipulates data in a logical manner. Further, the processor 502 may be similar to or include a processor that is similar to processor 160. The processor 502 is operable to execute programs, such as programs 506, 507. Thus, the processor 502 may be operable to operate the operations portion 514 or other aspects of the system 500 according to the instructions provided in the programs 506, 507. Consequently, in some implementations, the processor 502 is operable to control infusion of fluids into the eye and extraction of fluids therefrom in a manner similar to that described above. As such, the operations portion 514 may be operable to inject a retina manipulation fluid into an eye while maintaining a desired IOP within the eye.

Memory 504 includes one or more programs 506, including a fluid injection and extraction program 507. Programs 506 may be separate programs or parts (e.g., subroutines or libraries) of a larger program. Memory 504 may also include an operating system (e.g., Windows, Linux, or Unix). Memory 504 may include any memory or module and may take the form of volatile or non-volatile memory including, without limitation, magnetic media, optical media, random access memory (RAM), read-only memory (ROM), removable media, or any other suitable local or remote component for storing data.

Programs 506 may provide instructions for operating aspects of an injection/extraction technique, such as controlling of injection or a retinal manipulation fluid and a negative pressure to maintain a desired IOP.

Memory 504 may also store classes, frameworks, programs, backup data, jobs, or other information that includes any parameters, variables, algorithms, instructions, rules, or references thereto. Memory 504 may also include other types of data, such as environment and/or program description data, program data for one or more programs, as well as data involving virtual private network (VPN) programs or services, firewall policies, a security or access log, print or other reporting files, HyperText Markup Language (HTML) files or templates, related or unrelated software programs or sub-systems, and others. Consequently, memory 504 may also be considered a repository of data, such as a local data repository from one or more programs, such as program 507. Memory 504 may also include data that can be utilized by one or more programs, such as program 507.

Programs 506 may include a program or group of programs containing instructions operable to utilize received data, such as in one or more algorithms, to determine a result or output. The determined results may be used to affect an aspect of computer system 500. As indicated above, the operations portion 514 may include a fluid extraction system similar to the fluid extraction system 150 and/or a pressure system similar to pressure system 140. Further, in some implementations, the operations portion 514 may include additional, fewer, or different features. In some instances, program 507 may include instructions for controlling aspects of the fluid extraction system and the pressure system. Consequently, in some instances, the program 507 may include instructions for controlling aspects of an injection/extraction system that may be similar, for example, to injection/extraction system 300. Further, and program 507 may determine one or more adjustments to operations portion 514 to control aspects of the fluid injection/extraction system. For example, program 507 may provide instructions to cause the processor 502 to determine adjustments to a pressure level applied to a retinal manipulation fluid by a pressure system, such as pressure system 140 or a vacuum pressure level of a fluid extraction system, such as fluid extraction system 150. As such, the program 507 may cause the processor 502 to control the operations portion 514 such as to inject a retina manipulation fluid into an eye while maintaining a desired IOP within the eye. The adjustments may be implemented by one or more transmitted control signals to one or more components of computer system 500, such as operations portion 514.

Processor 502 executes instructions, such as the instructions contained in the applications 506 and 507, and manipulates data to perform the operations of the computer system 500, e.g., computational and logic operations, and may be, for example, a central processing unit (CPU), a blade, an application specific integrated circuit (ASIC), or a field-programmable gate array (FPGA).

The components of computer system 500 may be coupled to together by a network to allow them to communicate data therebetween. The network may, for example, include a number of different types of busses (e.g., serial and parallel).

Although FIG. 5 illustrates a single processor 502 in computer system 500, multiple processors 502 may be used according to particular needs, and reference to processor 502 is meant to include multiple processors 502 where applicable. For example, processor 502 may be adapted for receiving data from various components of the computer system 500 and/or devices coupled thereto, process the received data, and transmit data to one or more of the components of the system 500 and/or devices coupled thereto in response. In the illustrated embodiment, processor 502 executes program 507 for controlling aspects of a retinal surgery.

Further, processor 502 may transmit control signals to or receive signals from one or more components coupled thereto. For example, processor 502 may transmit control signals in response to received data. In some implementations, for example, processor 502 may execute programs 506 and transmit control signals to the operations portion 514 in response thereto.

Display 510 displays information to a user, such as a medical practitioner (e.g., physician). In some instances, display 510 may be a monitor for visually presenting information. In some instances, display 510 may operate both as a display and an input device. For example, display 510 may be a touch sensitive display in which a touch by a user or other contact with the display produces an input to computer system 500. Display 510 may present information to the user via the user interface 512.

User interface 512 may include a user interface operable to allow the user, such as a medical practitioner, to interface with the computer system 500 for any suitable purpose, such as viewing program or other system information. For example, user interface 512 could provide information associated with a medical procedure, including detailed information related to a vitreoretinal surgical procedure, operational aspects of probe 516, operations portion 514, or any other desired aspect of the computer system 500.

Generally, user interface 512 may provide a particular user with an efficient and user-friendly presentation of information received by, provided by, or communicated within computer system 500. User interface 512 may include a plurality of customizable frames or views having interactive fields, pull-down lists, and buttons operated by the user. User interface 512 may also present a plurality of portals or dashboards. For example, user interface 512 may display an interface that allows users to input and define parameters associated with probe 516.

It should be understood that the term user interface may be used in the singular or in the plural to describe one or more user interfaces and each of the displays of a particular user interface. Indeed, reference to user interface 512 may indicate a reference to the front-end or a component of one or more programs 506 without departing from the scope of this disclosure. Therefore, user interface 512 contemplates any user interface. For example, in some instances, user interface 512 may include a generic web browser for inputting data and efficiently presenting the results to a user. In other instances, user interface 512 may include a custom or customizable interface for displaying and/or interacting with the various features of one or more of the programs 506 or other system services.

In some implementations, computer system 500 may be in communication with one or more local or remote computers, such as computer 522, over a network 524. Computer system 500 may include one or more communication interfaces for performing the communication. A communication interface may, for instance, be a network interface card (whether wireless or wireless) or a modem.

Network 524 may facilitate wireless and/or wireline communication between computer system 500 and, generally, any other local or remote computer, such as computer system 522. For example, medical practitioners may use computer system 522 to interact with configurations, settings, and/or other aspects associated with operation of computer system 500, including the services associated with the programs 506. Network 524 may be all or a portion of an enterprise or a secured network. In another example, network 524 may be a VPN merely between computer system 500 and computer 522 across a wire and/or a wireless link. Example wireless links include IEEE 802.11, IEEE 802.20, WiMax, ZigBee, Ultra-Wideband, and many others. While illustrated as a single, continuous network, network 524 may be logically divided into various sub-nets or virtual networks without departing from the scope of this disclosure, so long as at least a portion of network 524 may facilitate communications among computer system 500, computer 522, and other devices.

For example, computer system 500 may be communicably coupled to a repository 526 through one sub-net while communicably coupled to computer 522 through another. In other words, network 524 encompasses any internal or external network, networks, sub-network, or combination thereof operable to facilitate communications between various computing components. Network 524 may communicate, for example, Internet Protocol (IP) packets, Frame Relay frames, Asynchronous Transfer Mode (ATM) cells, voice, video, data, and other suitable information between network addresses (collectively or interchangeably referred to as "information"). Network 524 may include one or more local area networks (LANs), radio access networks (RANs), metropolitan area networks (MANs), wide area networks (WANs), all or a portion of the global computer network known as the Internet, and/or any other communication system or systems at one or more locations. In certain embodiments, network 524 may be a secure network accessible to users via certain local or remote computer 522.

Computer 522 may be any computing device operable to connect or communicate with computer system 500 or network 524 using any communication link. As used in this disclosure, computer 522 is intended to encompass a personal computer, touch screen terminal, workstation, network computer, kiosk, wireless data port, smart phone, personal data assistant (PDA), one or more processors within these or other devices, or any other suitable processing device. In some instances, computer 522 may include an electronic computing device operable to receive, transmit, process, and store any appropriate data associated with computer system 500. Computer 522 may also include or execute a user interface 528. User interface 528 may be similar to user interface 512. It will be understood that there may be any number of computers 522 communicably coupled to computer system 500. Moreover, for ease of illustration, computer 522 is described in terms of being used by one user. But this disclosure contemplates that many users may use one computer or that one user may use multiple computers.

In certain modes of operation, processor 502, according to one or more programs 506, may determine whether to inject a retina manipulation fluid into an eye (e.g., upon receipt of a command through user input device 508). Once a retina manipulation fluid should be injected, processor 502 may generate a command for a pressure system (e.g., a hospital air supply system), which may cause the retina manipulation fluid to be injected. Processor 502 may also retrieve an IOP measurement and determine whether the measured IOP is satisfactory. If the IOP is not satisfactory, the processor may adjust an extraction pressure for a fluid injection/extraction system. The extraction pressure may, for example, be increased if the measured IOP is too high and decreased if the measured IOP is too low. Processor 502 may also perform a variety of other operations described above.

The terminology used herein is for the purpose of describing particular implementations only and is not intended to be limiting. As used herein, the singular form "a", "an", and "the" are intended to include the plural forms as well, unless the context clearly indicates otherwise. It will be further understood that the terms "comprises" and/or "comprising," when used in the this specification, specify the presence of stated features, integers, steps, operations, elements, and/or components, but do not preclude the presence or addition of one or more other features, integers, steps, operations, elements, components, and/or groups therefore.

The corresponding structure, materials, acts, and equivalents of all means or steps plus function elements in the claims below are intended to include any structure, material, or act for performing the function in combination with other claimed elements as specifically claimed. The description of the present implementations has been presented for purposes of illustration and description, but is not intended to be exhaustive or limited to the implementations in the form disclosed. Many modifications and variations will be apparent to those of ordinary skill in the art without departing from the scope and spirit of the disclosure. The implementations were chosen and described in order to explain the principles of the disclosure and the practical application and to enable others or ordinary skill in the art to understand the disclosure for various implementations with various modifications as are suited to the particular use contemplated.

A number of implementations have been described for retinal surgery, and several others have been mentioned or suggested. Moreover, those skilled in the art will readily recognize that a variety of additions, deletions, modifications, and substitutions may be made to these implementations while still performing retinal surgery. Thus, the scope of the protected subject matter should be judged based on the following claims, which may capture one or more concepts of one or more implementations.

The invention claimed is:

1. A system comprising:
    an injection and extraction system adapted to inject a retina manipulation fluid into an eye through a first channel and extract fluid from the eye through a second channel, the first channel extending distally beyond the second channel to form an annular opening between the first channel and the second channel;
    a fluid extraction system adapted to apply negative pressure to the injection and extraction system to facilitate fluid extraction;
    a computer system adapted to adjust the negative pressure applied by the fluid extraction system, and
    an infusion system adapted to inject infusion fluid to maintain the shape of the eye undergoing retinal surgery.

2. The system of claim 1, wherein the computer system is adapted to adjust the negative pressure based on intraocular pressure in the eye.

3. The system of claim 1, wherein the computer system is further adapted to control injection of the retina manipulation fluid through the injection and extraction system.

4. The system of claim 3, further comprising a fluid pressure system, the fluid pressure system controllable by the computer system to apply positive pressure to inject the retina manipulation fluid.

5. The system of claim 1, wherein the first channel is adapted to inject a fluid having a higher specific gravity than fluids for which the second channel is adapted to extract.

6. The system of claim 1, wherein the first channel is inside the second channel.

7. The system of claim 6, wherein the second channel serves as a cannula for introducing medical instruments into the eye.

8. The system of claim 1, wherein the injection and extraction system comprises a body through which the first channel passes and to which the second channel engages.

9. The system of claim 8, wherein the body comprises a cavity into which fluid extracted through the second channel enters.

10. A method, comprising:
    injecting a retina manipulation fluid into an eye through a first channel of an injection and extraction system that extends distally beyond a second channel to form an annular opening between the first channel and the second channel, the retinal manipulation fluid having a higher specific gravity than other fluids within the eye;
    applying negative pressure to the injection and extraction system to facilitate extraction of fluid from the eye through the annular opening;
    adjusting, via a computer system, the applied negative pressure; and
    extracting the other fluids from the eye.

11. The method of claim 10, wherein adjusting the negative pressure is based on intraocular pressure in the eye.

12. The method of claim 11, further comprising injecting fluid to maintain the shape of the eye.

13. The method of claim 11, further comprising measuring the intraocular pressure.

14. The method of claim 10, further comprising controlling injection of the retina manipulation fluid through the injection and extraction system via the computer system.

15. The method of claim 11, wherein the computer system controls a fluid pressure system to apply positive pressure to inject the retina manipulation fluid.

16. The method of claim 10, wherein:
    the extracted fluid is extracted around the first channel.

17. The method of claim 16, wherein the second channel serves as a cannula for introducing medical instruments into the eye.

18. The method of claim 16, wherein the retina manipulation fluid, while in the first channel, passes through a first internal cavity of the injection and extraction system.

19. The method of claim 18, wherein the extracted fluid enters a second internal cavity of the injection and extraction system after passing through the second channel.

* * * * *